US006245967B1

(12) United States Patent
Sonnewald et al.

(10) Patent No.: US 6,245,967 B1
(45) Date of Patent: Jun. 12, 2001

(54) PROCESS AND DNA MOLECULES FOR INCREASING THE PHOTOSYNTHESIS RATE IN PLANTS

(75) Inventors: Uwe Sonnewald, Hoym; Jens Kossmann, Golm; Botho Bowien, Gottingen, all of (DE)

(73) Assignee: Hoechst Schering Agrevo GmbH, Berlin (DE)

(*) Notice: Subject to any disclaimer, the term of this patent is extended or adjusted under 35 U.S.C. 154(b) by 0 days.

(21) Appl. No.: 08/860,820

(22) PCT Filed: Jan. 11, 1996

(86) PCT No.: PCT/EP96/00111

§ 371 Date: Sep. 4, 1997

§ 102(e) Date: Sep. 4, 1997

(87) PCT Pub. No.: WO96/21737

PCT Pub. Date: Jul. 18, 1996

(30) Foreign Application Priority Data

Jan. 13, 1995 (DE) .............................................. 195 02 053

(51) Int. Cl.[7] .......................... C12N 15/29; C12N 15/31; C12N 15/12; C12N 15/82
(52) U.S. Cl. .................... 800/278; 735/69.1; 735/320.1; 735/419; 735/468; 536/23.2; 536/23.5; 536/23.6; 536/23.7; 800/284; 800/288; 800/290; 800/289
(58) Field of Search ................................. 536/23.6, 24.1, 536/23.5, 23.2, 23.7; 800/205, DIG. 9, DIG. 67, 278, 284, 288, 290, 289, 295, 298; 435/252.37, 172.3, 419, 69.1, 468, 410, 320.1

(56) References Cited

PUBLICATIONS

Belknap et al. 1994. American potato Journal. 1994. vol. 7: 285–296.*
Carvalho et al. The EMBO Journal. 1992. vol. 11: 5995–5602).*
Schaewen et al. EMBO Journal. 1990. vol 9: 3033–3044.*
Gibson et al. (1990), "The Form II Fructose 1,6–Bisphosphatase and Phosphoribulokinase Genes Form Part of a Large Operon in *Rhodobacter sphaeroides*: Primary Structure and Insertional Mutagenesis Analysis", Biochemistry 29:8085–8093.
Genbank Accession No. J02922.
Raines et al. (1988), "Chloroplast Fructose–1,6–Bisphosphatase: The Product of a Mosaic Gene", Nucl. Acid. Res. 16:7931–7942.
Genbank Accession No. X58148.
Genbank Accession No. L15303.

Meijer et al. (1990), "Nucleotide sequences of the genes encoding fructosebisphosphatase and phosphoribulokinase from *Xanthobacter flavus* H4–14", J. Gen. Microbiol. 136:225–2230.
Hamilton et al. (1988), "Sequence of the *Escherichia coli* fructose–1, 6–bisphosphatase gene", Nucl. Acid. Res. 16:8707.
Genbank Accession No. L22884.
Rogers et al. (1988), "Characterization of the Gene for Fructose–1,6–bisphosphatase from *Saccharomyces cerevisiae* and *Schizosaccharomyces pombe*", J. Biol. Chem. 263:6051–6057.
Genbank Accession No. J03207.
Genbank Accession No. J03213.
El–Maghrabi et al. (1988), "cDNA sequence of rat liver fructose–1,6–bisphosphatase and evidence for down–regulation of its mRNA by insulin", Proc. Natl. Acad. Sci. 85:8430–8434.
Genbank Accession No. M86347.
El–Maghrabi et al. (1993), "Isolation of a Human Liver Fructose–1, 6–Bisphosphatase cDNA and Expression of the Protein in *Escherichia coli*", J. Biol. Chem. 268:9466–9472.
Genbank Accession No. M19922.
Genbank Accession No. L10320.
Hur et al. (1992), "Isolation and characterization of a cDNA encoding cytosolic fructose–1,6–bisphosphatase from spinach", Plant Mol. Biol. 18:799–802.
Genbank Accession No. M80597.
Genbank Accession No. X68826.
Genbank Accession No. X61690.
Genbank Accession No. X76946.
Sedivy et al. (1986), "AMP–insensitive fructose bisphosphatase in *Escherichia coli* and its consequences", Proc. Natl. Acad. Sci. 83:1656–1659.
Marcus et al. (1988), "Comparative amino acid sequence of fructose–1, 6–bisphosphatases: Identification of a region unique to the light–regulated chloroplast enzyme", Proc. Natl. Acad.Sci. 85:5379–5383.
Ladror et al. (1990), "Spinach cytosolic fructose–1,6–bisphosphatase: Purification, enzyme properties and structural comparisons", Eur. J. Biochem. 189:89–94.

(List continued on next page.)

*Primary Examiner*—David T. Fox
*Assistant Examiner*—Ousama Zaghmout
(74) *Attorney, Agent, or Firm*—Fish & Neave; James F. Haley, Jr.; Karen E. Brown

(57) ABSTRACT

The invention describes recombinant DNA molecules that allow expression of a deregulated or unregulated fructose-1,6-bisphosphatase (FBPase) in plant cells. Such expression leads to an increase in the photosynthesis rate and biomass production in photosynthetically active cells. Furthermore, the invention describes transgenic plants that show an increased photosynthesis rate due to the expression of a deregulated or unregulated FBPase.

20 Claims, 1 Drawing Sheet

OTHER PUBLICATIONS

Figure 1:
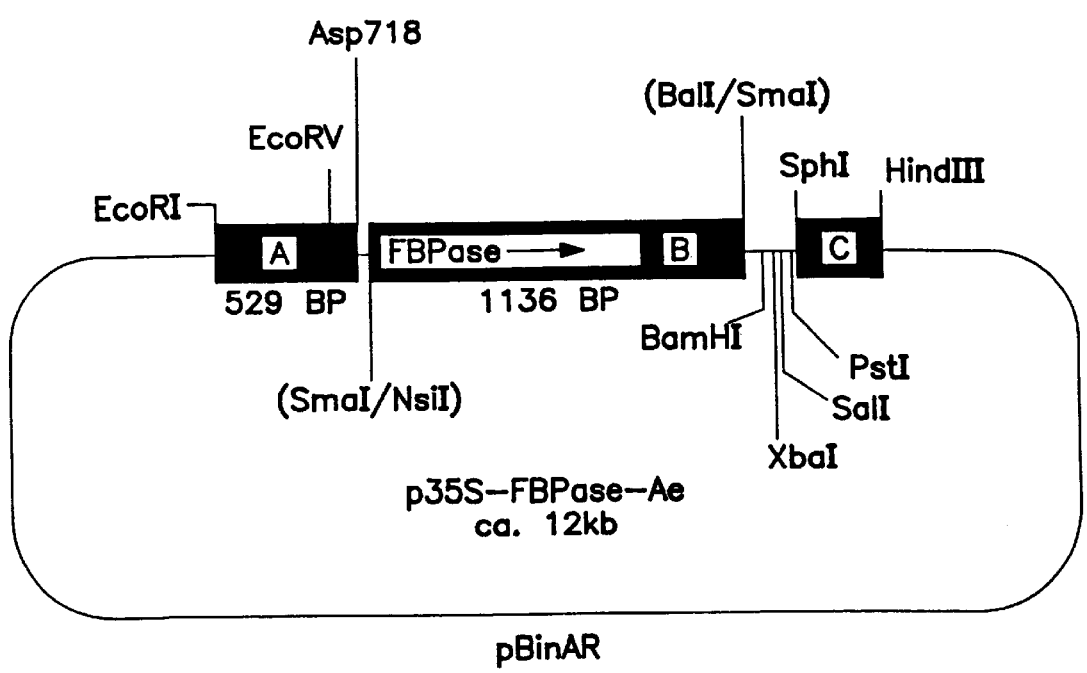

Ke et al. (1990), "Crystal structure of fructose–1,6–bisphosphatase complexed with fructose 6–phosphate, AMP, and magnesium", Proc. Natl. Acad. Sci. 87:5243–5247.

Ke et al. (1989), "Molecular structure of fructose–1, 6–bisphosphatase at 2.8–Å resolution", Proc. Natl. Acad. Sci. 86:1475–1479.

Chatterjee et al. (1985), "Des–1–25–fructose–1, 6–bisphosphatase, a Nonallosteric Derivative Produced by Trypsin Treatment of the Native Protein", J. Biol Chem. 260:13553–13559.

Ke et al. (1991), "Crystal structure of the neutral form of fructose–1,6–bisphosphatase complexed with the product fructose 6–phosphate at 2.1–Å resolution", Proc. Natl. Acad. Sci. 88:2989–2993.

Giroux et al. (1994), "Shared Active Sites of Fructose–1, 6–bisphosphatase", J. Biol. Chem. 269:31404–31409.

El–Maghrabi et al. (1992), "Lysine 274 Is Essential for Fructose 2, 6–Bisphosphate Inhibition of Fructose–1, 6–bisphosphatase", J. Biol. Chem. 267:6526–6530.

Sedivy et al. (1984), "Fructose Bisphosphatase of *Escherichia coli*: Cloning of the Structural Gene (*fbp*) and Preparation of a Chromosomal Deletion", J. Bacter. 158:1048–1053.

Amachi et al. (1979), "Characterization of Two Fructose Bisphosphatase Isoenzymes from the Hydrogen Bacterium *Nocardia opaca* 1b", J. Gen. Microbiol. 113:347–356.

Kossman, J. et al., "Sequence Analysis of the Chromosomal And Plasmid Genes Encoding Phosphoribulokinase From *Alcaligenes eutrophus*," *Gene*, pp. 247–252 (1989).

Koss mann, J. et al., "Reduction Of The Chloroplastic Fructose–1, 6–Bisphosphatase In Transgenic Potato Plants Impairs Photosynthesis And Plant Growth," *The Plant Journal*, 6, pp. 637–650 (1994).

San Juan, A. and Vasconcelos, A.C., "Overexpression Of Cytosolic Fructose–1,6 Bisphosphatase In Transgenic Tobacco Plants," *Supp. to Plant Phys.*, 105, pp. 32–889 (1994).

Windhöovel, U. and Bowien, B., "On The Operon Structure Of The *cfx*Gene Clusters In *Alcaligenes eutrophus*," *Arch Microbiol.*, 154, pp. 85–91 (1990).

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1136 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 30..1121

(xi) SEQUENCE DESCRIPTION: SEQ ID NO:1:

```
ATGCATAGCC AATCTATAGG AGACCTGTC ATG CCT GAA GTC CAA AGG ATG ACC          53
                                Met Pro Glu Val Gln Arg Met Thr
                                  1               5

CTG ACG CAG TTC CTG ATC GAG GAA CGC CGC CGC TAT CCG GAT GCC AGC         101
Leu Thr Gln Phe Leu Ile Glu Glu Arg Arg Arg Tyr Pro Asp Ala Ser
         10              15                  20

GGC GGC TTC AAC GGC CTG ATT CTC AAC GTC GCC ATG GCC TGC AAG GAA         149
Gly Gly Phe Asn Gly Leu Ile Leu Asn Val Ala Met Ala Cys Lys Glu
 25              30                  35                  40

ATC GCG CGC GCG GTT GCC TTC GGC GCG CTG GGG GGC TTG CAC GGC AAG         197
Ile Ala Arg Ala Val Ala Phe Gly Ala Leu Gly Gly Leu His Gly Lys
                 45                  50                  55

GCC AGC AAT CAA GCC GGA GAA GCA GGG GCC GTC AAC GTG CAG GGC GAA         245
Ala Ser Asn Gln Ala Gly Glu Ala Gly Ala Val Asn Val Gln Gly Glu
             60                  65                  70

ATC CAG CAG AAG CTG GAC GTG CTG AGC AAT ACC ACC TTC CTG CGC GTC         293
Ile Gln Gln Lys Leu Asp Val Leu Ser Asn Thr Thr Phe Leu Arg Val
         75                  80                  85

AAC GAG TGG GGC GGG TAC CTG GCC GGC ATG GCG TCG GAG GAG ATG GAG         341
Asn Glu Trp Gly Gly Tyr Leu Ala Gly Met Ala Ser Glu Glu Met Glu
 90                  95                 100

GCG CCT TAC CAG ATC CCG GAT CAC TAC CCG CGC GGC AAG TAC CTG CTG         389
Ala Pro Tyr Gln Ile Pro Asp His Tyr Pro Arg Gly Lys Tyr Leu Leu
105                 110                 115                 120

GTG TTC GAT CCG CTC GAC GGC TCA TCC AAC ATC GAC GTC AAT GTC TCG         437
Val Phe Asp Pro Leu Asp Gly Ser Ser Asn Ile Asp Val Asn Val Ser
                125                 130                 135

GTG GGC AGC ATC TTC TCG GTG CTG CGC GCG CCT GAG GGC GCA AGC GCC         485
Val Gly Ser Ile Phe Ser Val Leu Arg Ala Pro Glu Gly Ala Ser Ala
                140                 145                 150

GTC ACC GAG CAG GAT TTC CTG CAG CCC GGC AGC GCC CAG GTG GCG GCC         533
Val Thr Glu Gln Asp Phe Leu Gln Pro Gly Ser Ala Gln Val Ala Ala
            155                 160                 165

GGC TAC GCG CTC TAC GGT CCC ACC ACC ATG CTG GTG CTG ACC GTG GGC         581
Gly Tyr Ala Leu Tyr Gly Pro Thr Thr Met Leu Val Leu Thr Val Gly
        170                 175                 180

AAT GGC GTC AAC GGC TTC ACG CTC GAT CCC AAC CTG GGC GAG TTC TTC         629
Asn Gly Val Asn Gly Phe Thr Leu Asp Pro Asn Leu Gly Glu Phe Phe
185                 190                 195                 200
```

```
CTC ACG CAC CCC AAC CTG CAG GTG CCG GCC GAT ACC CAG GAA TTT GCC        677
Leu Thr His Pro Asn Leu Gln Val Pro Ala Asp Thr Gln Glu Phe Ala
            205                 210                 215

ATC AAT GCG TCG AAC AGC CGC TTC TGG GAA GCG CCG GTG CAG CGC TAC        725
Ile Asn Ala Ser Asn Ser Arg Phe Trp Glu Ala Pro Val Gln Arg Tyr
            220                 225                 230

ATC GCC GAG TGC ATG GCC GGC AAG AGC GGG CCG CGC GGC AAG GAT TTC        773
Ile Ala Glu Cys Met Ala Gly Lys Ser Gly Pro Arg Gly Lys Asp Phe
            235                 240                 245

AAT ATG CGC TGG ATC GCG TCG ATG GTG GCC GAG GCG CAC CGC ATC CTG        821
Asn Met Arg Trp Ile Ala Ser Met Val Ala Glu Ala His Arg Ile Leu
250                 255                 260

ATG CGT GGC GGC GTC TTC ATG TAC CCG CGC GAC TCC AAG GAT CCC GCC        869
Met Arg Gly Gly Val Phe Met Tyr Pro Arg Asp Ser Lys Asp Pro Ala
265                 270                 275                 280

AAG CCG GGC CGC CTG CGC CTG CTG TAC GAG GCC AAT CCG ATC GCC TTC        917
Lys Pro Gly Arg Leu Arg Leu Leu Tyr Glu Ala Asn Pro Ile Ala Phe
            285                 290                 295

CTG ATG GAG CAG GCT GGC GGG CGC GCC AGC ACG GGC CGG CAG ACG CTG        965
Leu Met Glu Gln Ala Gly Gly Arg Ala Ser Thr Gly Arg Gln Thr Leu
            300                 305                 310

ATG TCG GTG GCG CCG GGT GCG CTG CAC CAG CGC ATT GGC GTG ATC TTC       1013
Met Ser Val Ala Pro Gly Ala Leu His Gln Arg Ile Gly Val Ile Phe
            315                 320                 325

GGC TCG CGC AAT GAA GTG GAA CGG ATC GAG GGC TAC CAC ACC GAC CAG       1061
Gly Ser Arg Asn Glu Val Glu Arg Ile Glu Gly Tyr His Thr Asp Gln
330                 335                 340

ACC GAT CCC GAC CTT CCG AGT CCC CTG TTC AAC GAG CGC AGC CTG TTC       1109
Thr Asp Pro Asp Leu Pro Ser Pro Leu Phe Asn Glu Arg Ser Leu Phe
345                 350                 355                 360

CGC GCG TCT GCC TGAGGTGCCT GGCCA                                      1136
Arg Ala Ser Ala (2) INFORMATION FOR SEQ ID NO:2:

(i) SEQUENCE CHARACTERISTICS:
        (A) LENGTH: 364 amino acids
        (B) TYPE: amino acid
        (D) TOPOLOGY: linear (ii) MOLECULE TYPE: protein (xi) SEQUENCE DESCRIPTION: SEQ ID NO:2:

Met Pro Glu Val Gln Arg Met Thr Leu Thr Gln Phe Leu Ile Glu Glu
  1               5                  10                  15

Arg Arg Arg Tyr Pro Asp Ala Ser Gly Gly Phe Asn Gly Leu Ile Leu
                 20                  25                  30

Asn Val Ala Met Ala Cys Lys Glu Ile Ala Arg Ala Val Ala Phe Gly
             35                  40                  45

Ala Leu Gly Gly Leu His Gly Lys Ala Ser Asn Gln Ala Gly Glu Ala
     50                  55                  60

Gly Ala Val Asn Val Gln Gly Glu Ile Gln Lys Leu Asp Val Leu
 65                  70                  75                  80

Ser Asn Thr Thr Phe Leu Arg Val Asn Glu Trp Gly Gly Tyr Leu Ala
                 85                  90                  95

Gly Met Ala Ser Glu Glu Met Glu Ala Pro Tyr Gln Ile Pro Asp His
                100                 105                 110

Tyr Pro Arg Gly Lys Tyr Leu Leu Val Phe Asp Pro Leu Asp Gly Ser
            115                 120                 125
```

```
Ser Asn Ile Asp Val Asn Val Ser Val Gly Ser Ile Phe Ser Val Leu
    130                 135                 140
Arg Ala Pro Glu Gly Ala Ser Ala Val Thr Glu Gln Asp Phe Leu Gln
145                 150                 155                 160
Pro Gly Ser Ala Gln Val Ala Ala Gly Tyr Ala Leu Tyr Gly Pro Thr
                165                 170                 175
Thr Met Leu Val Leu Thr Val Gly Asn Gly Val Asn Gly Phe Thr Leu
                180                 185                 190
Asp Pro Asn Leu Gly Glu Phe Phe Leu Thr His Pro Asn Leu Gln Val
            195                 200                 205
Pro Ala Asp Thr Gln Glu Phe Ala Ile Asn Ala Ser Asn Ser Arg Phe
            210                 215                 220
Trp Glu Ala Pro Val Gln Arg Tyr Ile Ala Glu Cys Met Ala Gly Lys
225                 230                 235                 240
Ser Gly Pro Arg Gly Lys Asp Phe Asn Met Arg Trp Ile Ala Ser Met
                245                 250                 255
Val Ala Glu Ala His Arg Ile Leu Met Arg Gly Gly Val Phe Met Tyr
            260                 265                 270
Pro Arg Asp Ser Lys Asp Pro Ala Lys Pro Gly Arg Leu Arg Leu Leu
            275                 280                 285
Tyr Glu Ala Asn Pro Ile Ala Phe Leu Met Glu Gln Ala Gly Gly Arg
    290                 295                 300
Ala Ser Thr Gly Arg Gln Thr Leu Met Ser Val Ala Pro Gly Ala Leu
305                 310                 315                 320
His Gln Arg Ile Gly Val Ile Phe Gly Ser Arg Asn Glu Val Glu Arg
                325                 330                 335
Ile Glu Gly Tyr His Thr Asp Gln Thr Asp Pro Asp Leu Pro Ser Pro
                340                 345                 350
Leu Phe Asn Glu Arg Ser Leu Phe Arg Ala Ser Ala
            355                 360
```

PROCESS AND DNA MOLECULES FOR INCREASING THE PHOTOSYNTHESIS RATE IN PLANTS

This application is filed under 35 U.S.C. §371 as a national stage application of the International application PCT/EP96/00111, filed Jan. 11, 1996, and is entitled to priority under 35 U.S.C. §119 to German patent application 195 02 053.7, filed Jan. 13, 1995.

The present invention relates to a process and DNA molecules for increasing the photosynthesis rate in plants as well as for an increased yield of plants. The photosynthesis rate and/or the yield is increased by the expression of a deregulated or unregulated fructose-1,6-bisphosphatase in the cytosol of transgenic plants. The invention also relates to the plant cells and plants obtainable by this process as well as to the use of DNA sequences coding for proteins having the enzymatic activity of a fructose-1,6-bisphosphatase for the production of plants exhibiting an increased photosynthesis rate. The invention furthermore relates to recombinant DNA molecules leading to the expression of a fructose-1,6-bisphosphatase in plant cells and plants and resulting in an increased photosynthesis rate.

Due to the continuously growing need for food which is a result from the ever-growing world population it is one of the objects of research in the field of biotechnology to try to increase the yields of useful plants. One possibility to attain this object is to genetically engineer the metabolism of plants. Respective targets are, e.g., the primary processes of photosynthesis that result in $CO_2$ fixation, the transport processes that participate in the distribution of the photoassimilates within the plant, but also the metabolic pathways that lead to the synthesis of storage substances such as starch, proteins or fats.

For example, the expression of a procaryotic asparagine synthetase in plant cells has been described which results in transgenic plants inter alia in an increase in biomass production (EP 0 511 979).

Another proposal has been to express a procaryotic polyphosphate kinase in the cytosol of transgenic plants. Such expression results in potato plants in an increase in yield in terms of tuber weight of up to 30%.

EP-A-0 442 592 describes the expression of an apoplastic invertase in potato plants which leads to a modified yield of transgenic plants so modified.

Further approaches have concentrated on a modification of the activities of enzymes that participate in the synthesis of sucrose, the most important transport metabolite in most plant species. In plants the $CO_2$ fixed in the course of photosynthesis is transported from the plastids to the cytosol in the form of triosephosphates (glyceraldehyde-3-phosphate and dihydroxyacetone phosphate). In the cytosol the enzyme aldolase forms a molecule of fructose-1,6-bisphosphate by condensation of glyceraldehyde-3-phosphate and dihydroxyacetone phosphate. This molecule is converted into a molecule of fructose-6-phosphate which in turn is the substrate for the synthesis of sucrose phosphate by the enzyme sucrose phosphate synthase according to the equation

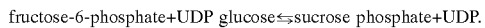
fructose-6-phosphate+UDP glucose⇌sucrose phosphate+UDP.

The conversion of fructose-1,6-bisphosphate into fructose-6-phosphate is catalyzed by the enzyme fructose-1,6-bisphosphatase (in the following: FBPase; EC 3.1.3.11) which is regulated by various substances. For example, fructose-2,6-bisphosphate and AMP are potent inhibitors of said enzyme. AMP is an allosteric inhibitor, while fructose-2,6-bisphosphate binds to the active center of the enzyme (Ke et al., Proc. Natl. Acad. Sci. USA 86 (1989), 1475–1479; Liu et al., Biochem. Biophys. Res. Comm. 161 (1989), 689–695. Plant cells contain both a cytoplasmatic as well as a chloroplastic FBPase coded for by the nuclear genome. The reverse reaction (conversion of fructose-6-phosphate into fructose-1,6-bisphosphate) is catalyzed by the enzyme phospho-fructokinase (PFK) using ATP. Said enzyme is activated by fructose-6-phosphate, $P_i$ and fructose-2,6-bisphosphate and inhibited by glyceraldehyde-3-phosphate and dihydroxyacetone phosphate. Besides said enzymes another enzyme is present in plant cells, namely pyrophosphate:fructose-6-phosphate-1-phosphotransferase (PFP) which catalyzes both reactions according to the equation:

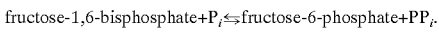
fructose-1,6-bisphosphate+$P_i$⇌fructose-6-phosphate+$PP_i$.

So far various attempts have been made to manipulate this step in the synthesis of sucrose such that the amount of $CO_2$ fixed is increased resulting in an increased biomass production. For example, it has been attempted to increase the production of fructose-1,6-bisphosphate by overexpressing a plant FBPase in the cytosol (Juan et al., Supplement to Plant Physiol., Vol. 105 (1994), 118). However, this does not lead to a measurable increase of sucrose synthesis. Antisense-inhibition of the PFP, too, failed to result in a detectable increase of sucrose synthesis in plant cells (Hajirezaei et al., Planta 192 (1994), 16–30). It has been furthermore attempted to influence the reaction catalyzed by FBPase by modifying the concentration of the allosteric inhibitor fructose-2,6-bisphosphate (Kruger and Scott, Biochemical Society Transactions, Transgenic Plants and Plant Biochemistry 22 (1994), 904–909). However, it has been found that an increase in the fructose-2,6-bisphosphate concentration has no effect on the photosynthesis rate and only a minor effect on the synthesis of starch or sucrose.

The problem underlying the present invention is to provide further processes generally useful in plants that allow an increase of the photosynthesis rate in plants und thus an increase in biomass production and yield.

The problem is solved by the provision of the embodiments characterized in the claims.

The invention relates to recombinant DNA molecules containing
(a) a promoter functional in plant cells and
(b) a DNA sequence linked with the promoter in sense orientation which codes for a polypeptide having the enzymatic activity of a fructose-1,6-bisphosphatase,
with the polypeptide having the enzymatic activity of a fructose-1,6-bisphosphatase being a deregulated or unregulated enzyme.

It has surprisingly been found that by expression of such DNA molecules in plant cells a dramatic increase in the photosynthesis rate in plants so modified can be achieved vis-à-vis wild type plants. The term "deregulated" means that said enzymes are not regulated in the same manner as the FBPase enzymes normally expressed in plant cells. Specifically, these enzymes are subject to other regulatory mechanisms, i.e., they are not inhibited to the same extent by the inhibitors or activated by the activators which normally inhibit or activate plant FBPases. For example, they are not inhibited by fructose-2,6-bisphosphate or AMP to the same extent as FBPases that are normally present in plants.

The term "unregulated FBPase enzymes" as used in the present invention relates to FBPase enzymes that are not subject to regulatory mechanisms in plant cells, specifically to those that are not regulated by AMP, ATP or fructose-2,6-bisphosphate.

An increased photosynthesis rate means that plants that have been transformed with a DNA molecule according to the invention which leads to the synthesis of a deregulated or unregulated FBPase in the plants exhibit an increased photosynthesis rate vis-à-vis non-transformed plants, preferably a photosynthesis rate that is increased by at least 10%, particularly a photosynthesis rate that is increased by at least 20%, most preferably a photosynthesis rate that is increased by 30–40%.

The promoter contained in the DNA molecules according to the invention in principle may be any promoter functional in plant cells. The expression of the DNA sequence coding for an unregulated or deregulated FBPase in principle may take place in any tissue of a transformed plant and at any point in time, preferably it takes place in photosynthetically active tissues. An example for an appropriate promoter is the 35S promoter of the cauliflower mosaic virus (Odell et al., Nature 313 (1985), 810–812) which allows constitutive expression in all tissues of a plant. However, promoters may be used that lead to the expression of subsequent sequences only in a certain tissue of the plant, preferably in photosynthetically active tissue (see, e.g., Stockhaus et al., EMBO J. 8 (1989), 2245–2251) or at a point in time determinable by external influences (see, e.g., WO93/07279). Beside the promoter a DNA molecule according to the invention may also contain DNA sequences that guarantee further increase of the transcription, for example so-called enhancer elements, or DNA sequences that are located in the transcribed region and guarantee a more efficient translation of the synthesized RNA into the corresponding protein. Such 5'-nontranslated regions may be obtained from viral genes or suitable eucaryotic genes or may be synthetically produced. They may be homologous or heterologous with respect to the promoter used.

Furthermore, the DNA molecules according to the invention may contain 3'-nontranslated DNA sequences that guarantee transcription termination and polyadenylation of the transcript formed. Such termination signals are known and have been described. They are freely interchangeable. Examples for such termination sequences are the 3'-nontranslated regions including the polyadenylation signal of the nopaline synthase gene (NOS gene) from agrobacteri or the 3'-nontranslated regions of the genes of the small subunit of ribulose-1,5-bisphosphate carboxylase (ssRUBISCO).

The DNA sequence coding for a polypeptide having the enzymatic activity of an FBPase may be derived from any organism expressing such enzyme. These DNA sequences are preferably DNA sequences coding for FBPase enzymes which, vis-à-vis the FBPase enzymes occurring in wild type plant, are subject to a modified, preferably a reduced regulation by inhibitors, particularly a reduced allosteric regulation. The enzymes coded for by the sequences may be know, naturally occurring enzymes exhibiting a modified regulation by various substances, or enzymes that have been produced by mutagenesis of known enzymes from bacteria, algae, fungi, animals or plants. Particularly, they may be fragments of such enzymes that still exhibit the enzymatic activity of an FBPase, which, however, are deregulated or unregulated vis-à-vis FBPases that naturally occur in plant cells.

In a preferred embodiment of the present invention the DNA sequence coding for a polypeptide having the enzymatic activity of an FBPase is derived from a procaryotic organism, preferably a bacterial organism. Bacterial FBPases are advantageous in that they are not regulated by fructose-2,6-bisphosphate vis-à-vis plant derived FBPases. Many bacterial FBPases in contrast to the p ant and animal derived FBPases are not regulated in their enzymatic activity by AMP. It is preferred to use DNA sequences coding for such FBPases.

In another preferred embodiment the DNA molecules according to the invention contain a DNA sequence from *Alcaligenes eutrophus* coding for a fructose-1,6-bisphosphatase, preferably a DNA sequence exhibiting the coding region depicted under Seq ID No. 1. The FBPase enzyme from *Alcaligenes eutrophus* having the amino acid sequence indicated under Seq ID No. 1 in contrast to plant and animal derived FBPase enzymes is not inhibited by AMP (Abdelal and Schlegel, J. Bacteriol. 120 (1974), 304–310). The DNA sequence depicted under Seq ID No. 1 is a chromosomal DNA sequence. Beside said FBPase *Alcaligenes eutrophus* has a FBPase coded for by a plasmid (J. Koβmann; thesis, 1988, Georg-August-Universität, Göttingen, Germany).

Beside the above-mentioned DNA sequence from *Alcaligenes eutrophus* further bacterial DNA sequences are known that code for polypeptides having the enzymatic activity of an FBPase and that may be used to construct the DNA molecules according to the invention due to their properties. For example, the cfxF gene from *Xanthobacter flavus* H4-14 (Meijer et al., J. Gen. Microbiol. 136 (1990), 2225–2230; Meijer et al., Mol. Gen. Genet. 225 (1991), 320–330) as well as the fbp gene from *Rhodobacter sphaeroides* (Gibson et al., Biochemistry 29 (1990), 8085–8093; GenEMBL data base: accession no. J02922) have been cloned. The fbp gene from *Rhodobacter sphaeroides* is particularly suitable since the FBPase enzyme coded for by said gene is not inhibited by AMP.

Furthermore, the DNA sequence of the fbp gene from *Escherichia coli* coding for FBPase is known (Sedivy et al., J. Bacteriol. 158 (1984), 1048–1053; Hamilton et al. Nucl. Acids Res. 16 (1988), 8707; Raines et al., Nucl. Acids Res. 16 (1988), 7931–7942), as well as a mutated FBPase that is insensitive to AMP (Sedivy et al., Proc. Natl. Acad. Sci. USA 83 (1986), 1656–1659).

Furthermore known is a DNA sequence from *Nitrobacter vulgaris* coding for an FBPase (GenEMBL data base: accession no. L22884) and that may also be used to construct the DNA molecules according to the invention.

In another preferred embodiment the DNA molecules according to the invention contain DNA sequences from fungi coding for an FBPase. DNA sequences coding for FBPase are known from, e.g., *Saccharomyces cerevisiae* and *Schizosaccharomyces pombe* (Rogers et al., J. Biol. Chem. 263 (1988), 6051–6057; GenEMBL data base: accession nos. J03207 and J03213).

In another preferred embodiment the DNA molecules according to the invention contain DNA sequences from animal organisms coding for an FBPase, preferably DNA sequences from mammals. For example, from mammals a cDNA sequence is known which codes for the FBPase from rat liver (El-Maghrabi et al., Proc. Natl. Acad. Sci. USA 85 (1988), 8430–8434) as well as cDNA sequences coding for an FBPase from pig liver and pig kidney (Marcus et al., Proc. Natl. Acad. Sci. USA 79 (1982), 7161–7165; Williams et al., Proc. Natl. Acad. Sci. USA 89 (1992), 3080–3082; Burton et al., Biochem. Biophys. Res. Commun. 192 (1993), 511–517; GenEMBL data base: accession no. M86347). Furthermore known is a cDNA sequence coding for an FBPase from humans (El-Maghrabi, J. Biol. Chem. 268 (1993), 9466–9472; GenEMBL data base: accession nos. M19922 and L10320).

In a further -preferred embodiment the DNA molecules according to the invention contain a plant-derived DNA sequence coding for an FBPase. Such sequences are likewise known. For example, Hur et al. (Plant Mol. Biol. 18 (1992), 799–802) describe a cDNA coding for the cytosolic FBPase from spinach. Said enzyme has been extensively examined on the biochemical level (Zimmermann et al., J. Biol. Chem. 253 (1978), 5952–5956; Ladror et al., Eur. J. Biochem. 189 (1990), 89–94). Raines et al. (Nucl. Acids Res. 16 (1988), 7931–7942) describe a cDNA sequence coding for the chloroplast FBPase from wheat. A genomic DNA sequence coding for said enzyme is also described (Lloyd et al., Mol. Gen. Genet. 225 (1991), 209–216). Furthermore known are cDNA sequences coding for FBPases from *Arabidopsis thaliana* (GenEMBL data base: accession no. X58148), *Beta vulgaris* (sugar beet; GenEMBL data base: accession no. M80597), *Brassica napus* (GenEMBL data base: accession no. L15303), *Pisum sativum* (GenEMBL data base: accession no. X68826), *Spinacia oleracea* (GenEMBL data base: accession no. X61690) and *Solanum tuberosum* (GenEMBL data base: accession no. X76946).

The above-described DNA sequences coding for FBPase enzymes can be used to isolate further DNA sequences from other organisms, employing, e.g., conventional methods such as screening cDNA libraries or genomic libraries with appropriate probes.

DNA sequences coding for FBPase enzymes, which in comparison to FBPases naturally occurring in plant cells are not deregulated or unregulated, can be modified with the help of techniques known to the person skilled in the art such that the proteins coded for are deregulated or unregulated. Thus, the DNA molecules according to the invention may comprise DNA sequences which are derived from DNA sequences from procaryotic, plant or animal organisms or from fungi coding for an FBPase. This fact is explained in more detail in the following.

Apart from DNA sequences coding for FBPase enzymes also FBPase enzymes have been purified, biochemically characterized and partially sequenced from a large number of organisms, e.g., the cytosolic and the chloroplast FBPase from spinach (Zimmermann et al., J. Biol. Chem. 253 (1978), 5952–5956; Ladror et al., Eur. J. Biochem. 189 (1990), 89–94; Zimmermann et al., Eur. J. Biochem. 70 (1976), 361–367; Soulié et al., Eur. J. Biochem. 195 (1991), 671–678; Marcus and Harrsch, Arch. Biochem. Biophys. 279 (1990), 151–157; Marcus et al., Biochemistry 26 (1987), 7029–7035), the FBPase from maize (Nishizawa and Buchanan, J. Biol. Chem. 256 (1981), 6119–6126), the chloroplast FBPase from wheat (Leegood and Walker, Planta 156 (1982), 449–456), the FBPase from *Synechococcus leopoliensis* (Gerbling et al., Plant Physiol. (1986), 716–720), from *Polysphondylium pallidum* (Rosen, Arch. Biochem. Biophys. 114 (1966), 31–37), from rabbit liver (Pontremoli et al., Arch. Biochem. Biophys. 114 (1966), 24–30), from pig (Marcus et al., Proc. Natl. Acad. Sci. USA 79 (1982), 7161–7165), from *Rhodopseudonomas palustris* (Springgate and Stachow, Arch. Biochem. Biophys. 152 (1972), 1–12; Springgate and Stachow, Arch. Biochem. Biophys. 152 (1972), 13–20), from *E. coli* (Fraenkel et al., Arch. Biochem. Biophys. 114 (1966), 4–12) as well as two isoforms from *Nocardia opaca* 1b (Amachi and Bowien, J. Gen. Microbiol. 113 (1979), 347–356).

Furthermore, for the FBPases from pig the crystal structures of the complexes of the enzymes were determined with fructose-6-phosphate, AMP, fructose-2,6-bisphosphate and magnesium (Seaton et al., J. Biol. Chem. 259 (1984), 8915–8916; Ke et al., Proc. Natl. Acad. Sci. USA 87 (1990), 5243–5247; Ke et al., J. Mol. Biol. 212 (1989), 513–539; Ke et al., Proc. Natl. Acad. Sci. USA 88 (1991), 2989–2993; Ke et al., Biochemistry 30 (1991), 4412–4420). In so doing, the binding sites of fructose-6-phosphate and AMP could be identified as well as the amino acid residues interacting with these substances. Furthermore, it has been described for the FBPases from pig that the removal of the nucleotides coding for amino-acid residues 1–25 leads to the synthesis of an FBPase that is not inhibited by AMP but retains its catalytic properties (Chatterjee et al., J. Biol. Chem. 260 (1985), 13553–13559). DNA sequences coding for such FBPases are preferably used in the present invention.

Sequence comparisons on the level of the nucleotide sequences of the FBPase genes as well as on the level of the amino acid sequence of the FBPase enzymes have likewise been made in large numbers (Marcus et al., Biochem. Biophys. Res. Comm. 135 (1986), 374–381). The result was that certain domains of the FBPase have been relatively highly conserved even between remotely related organisms (Gibson et al., Biochemistry 29 (1990), 8085–8093; Marcus et al., Proc. Natl. Acad. Sci. USA 85 (1988), 5379–5383; Rogers et al., J. Biol. Chem. 263 (1988), 6051–6057). It could, for instance, be shown that the amino acid residues that form the catalytic center in the FBPase from pig are highly conserved in the FBPase from *Xanthobacter flavus* (Meijer et al., J. Gen. Microbiol. 136 (1990), 2225–2230).

The sequence comparisons of the amino acid sequence of the FBPase from *Rhodobacter sphaeroides*, too, with the sequences of other FBPase enzymes known so far indicate conserved regions as well as amino acid residues that participate in the catalysis or the regulation of enzyme activity (Gibson et al., Biochemistry 29 (1990), 8085–8093).

The regulation of the FBPase enzymes has likewise been extensively examined and described in detail (Tejwani, Advances in Enzymology, Vol. 54 (1983), 121–194).

Altogether, the data known so far for DNA sequences coding for FBPase enzymes, for amino acid sequences of FBPase enzymes, for crystal structures as well as for the regulatory and for kinetic and biochemical properties of the FBPases known so far give such a detailed picture that it is possible with this information to specifically introduce mutations into available DNA sequences that result in a modified regulation of the enzyme activity of the synthesized protein. As already mentioned above, it is, e.g., possible to remove the inhibition by AMP in the FBPase from pig by deleting the 25 N-terminal amino acids of the enzyme. The catalytic activity of the enzyme is not influenced by this deletion. Due to the high degree of conservation of the FBPase genes it should therefore be possible to evoke an insensitivity to AMP in other FBPase enzymes, too, by deleting a sufficiently long region at the N-terminus of the enzyme.

It is furthermore known for chromosomally or plasmid encoded FBPases from *Alcaligenes eutrophus* that the plasmidarily encoded enzyme has a characteristic ATP binding site that is missing in the chromosomally encoded enzyme. The plasmid encoded FBPase exhibits in its amino acid sequence the motif GQCMAGKS which is missing in the chromosomally encoded FBPase. This sequence has been identified as or is discussed as an ATP binding site for the phosphoribulokinase and many other enzymes. The detected consensus sequence (GXXXXGKT/S) is completely contained in the above-mentioned sequence. It is possible that this sequence is responsible for the binding of ATP and thus for the inhibition of the enzyme activity by ATP, such as is observed in various bacterial FBPases.

It is therefore possible to screen bacterial DNA sequences coding for FBPases and being inhibited by ATP for the presence of comparable ATP binding sites and to inactivate or remove this ATP binding site by techniques known in molecular biology and to thus produce an enzyme that cannot be inhibited by ATP.

In a similar manner the sensitivity to the inhibitor fructose-2,6-bisphosphate may be modified. The data obtained by X-ray structure analysis for crystals of the FBPase from pig as well as the analysis of various mutants have meanwhile made it possible to characterize the binding site for fructose-2-bisphosphate in the active center of the FBPase. For FBPase from pig, e.g., amino acid residues have been modified by site-directed mutagenesis, which appear to be important for the function of the enzyme due to the structural data obtained (Giroux et al., J. Biol. Chem. 269 (1994), 31404–31409 and the pertaining references). It could be shown that the amino acid arginine 243 of the FBPase from pig kidney participates in the substrate binding as well as in the inhibition by fructose-2,6-bisphosphate. By replacing this amino acid by an alanine residue a functional FBPase enzyme could be produced whose affinity for fructose-2,6-bisphosphate is reduced by a factor of 1,000 as compared to the wild type enzyme whereas affinity for the substrate fructose-1,6-bisphosphate is only reduced by a factor of 10 (Giroux et al., J. Biol. Chem. 269 (1994), 31404–31409). It could be furthermore shown for FBPase from rat liver that removal of a lysine residue in the active center which residue is also essential for the binding of fructose-1,6-bisphosphate and fructose-2,6-bisphosphate, results in an enzyme that possesses an affinity to the inhibitor fructose- 2,6-bisphosphate that is reduced by the factor of 1,000 (El-Maghrabi et al., J. Biol. Chem. 267 (1992), 6526–6530). Mutagenization of the relevant amino acid residues should therefore also allow the production of mutants that are modified in their control by fructose-2,6-bisphosphate vis-à-vis wild type proteins. Due to the high degree of conservation of the amino acid sequence of the FBPase enzymes, particularly in the area of the active center, it should furthermore be possible to apply the results obtained for mutants of the enzyme of a certain organism to enzymes that are derived from other organisms.

A further possibility of identifying amino acid residues essential for the catalysis as well as for the inhibition by fructose-2,6-bisphosphate is the computer-aided simulation of the molecular structure. Amino acid residues that are identified as being relevant can subsequently be specifically modified by site-directed mutagenesis and mutants can be examined for their properties.

For a particularly efficient increase of the photosynthesis rate or of the synthesis of fructose-6-phosphate from fructose-1,6-bisphosphate FBPase enzymes are used that are subject only to a reduced regulation by the inhibitors of plant FBPase enzymes (deregulated FBPase enzymes), preferably by enzymes that are no longer subject to any regulation (unregulated FBPase enzymes). Their catalytic activity, however, remains largely untouched. The coding regions of FBPase genes from bacteria, fungi, animals or plants can be mutagenized in E. coli or any other suitable host according to methods known in the art and can subsequently be analyzed for an increased FBPase activity and the regulatory mechanisms. The introduction of mutations can be performed in a specific manner (e.g., by site-directed mutagenesis) using specific oligonucleotides, or unspecifically. In the case of unspecific mutagenesis there is the possibility of amplifying the respective DNA sequences by polymerase chain reaction in the presence of $Mn^{2+}$ ions instead of $Mg^{2+}$ ions, where the error rate is increased, or the propagation of the respective DNA molecules in the E. coli strain XL1-Red which results in a high error rate during replication of the plasmid DNA introduced into the bacteria.

The mutagenized DNA sequences coding for the FBPase enzymes are subsequently introduced for analysis of the FBPase activity into a suitable host, preferably into an FBPase-deficient E. coli strain. An example of such a strain is E. coli strain DF657 (Sedivy et al., J. Bacteriol. 158 (1984),1048–1053). For an identification of clones expressing a functional FBPase enzyme the transformed cells are plated onto minimal medium containing, e.g., glycerol and succinate (each in a concentration of 0.4%) as carbon source. Cells that do not express functional FBPase cannot grow on such a medium. A first pointer to the activity of the expressed FBPase can be the growth rates of transformed viable clones. In order to preclude mutations in the promoter region resulting in an increased FBPase activity, the mutated coding DNA sequences that allow growth on a minimal medium have to be recloned into non-mutagenated vectors and again be screened for FBPase activity (again by complementation of a FBPase deficient E. coil strain). Mutants that effect a complementation of an FBPase deficient E. coli strain even in the second screening round are used for the analysis of FBPase activity in the presence of various inhibitors and activators.

The respective cells are broken up, and the FBPase activity is detected in vitro using an enzymatic test. In such a test the buffer in which the test is performed for analyzing the properties of the FBPase that was mutagenated is chosen such that the pH value and the salt concentrations are in the optimum range. The buffer must furthermore contain the substrate fructose-1,6-bisphosphate (about 1 mM) and $MgCl_2$ (about 5 mM). If plant and animal FBPases are expressed, an SH protection group reagent such as DTT or β-mercaptoethanol should be present in the buffer. The measurement of the enzyme activity is based on that two other enzymes, phosphoglucose isomerase and glucose-6-phosphate dehydrogenase from yeast which further react the product of the FBPase reaction, the fructose-6-phosphate, as well as NADP are added to the mixture. The phosphoglucose isomerase transfers fructose-6-phosphate into glucose-6-phosphate which in turn is reacted from glucose-6-phosphate dehydrogenase to give 6-phosphoglucono-δ-lactone while forming NADPH. The increase in NADPH can be photometrically determined by measuring the absorption at 334 nm. This increase also allows to determine the FBPase activity.

By adding various inhibitors (AMP, ATP, fructose-2,6-bisphosphate) the influence of the inhibitors on the enzyme activity of the mutated FBPases can be determined with the enzyme test described above.

By comparing these values with the values for the activity of the non-mutated enzyme suitable mutants can be chosen. DNA sequences coding for the deregulated or unregulated mutated proteins can subsequently be used to construct the DNA molecules according to the invention.

The generation of mutations in FBPase genes as well as the selection of suitable mutants in an FBPase deficient E. coli strain can also be carried out as described in Sedivy et al. (Proc. Natl. Acad. Sci. USA 83 (1986), 1656–1659). This process already allowed to isolate an AMP-insensitive FBPase.

According to the invention the deregulated or unregulated FBPase may be located in any desired compartment of the plant cells. In preferred embodiments the deregulated or unregulated FBPase is located in the cytosol or in the plastides of plant cells. Methods to construct DNA molecules which ensure the localization of a desired protein in various compartments of plant cells, namely in the cytosol or the plastides, are well known to the person skilled in the art.

Another subject matter of the present invention are transgenic plant cells that are transformed with an above-described DNA molecule according to the invention, or that are derived from such a transformed cell and contain a recombinant DNA molecule according to the invention, preferably stably integrated into their genome. The transgenic plant cells are preferably photosynthetically active cells.

The transgenic cells according to the invention can be used to regenerate whole transgenic plants.

Therefore, the present invention also relates to transgenic plants containing the transgenic plant cells according to the invention. Expression of a deregulated or unregulated FBPase in the cells of said plants results in an increase in the photosynthesis rate, thereby leading to an increase in biomass production and/or in yield as compared to non-transformed plants.

The transgenic plants according to the invention are preferably produced by introducing a DNA molecule according to the invention into plant cells and regenerating whole plants from the transformed cells.

The transfer of a DNA molecule according to the invention into plant cells is preferably performed using suitable plasmids, particularly plasmids that allow stable integration of the DNA molecule into the genome of transformed plant cells, e.g., of binary plasmids. Suitable plant transformation vectors comprise, e.g., vectors derived from the Ti plasmid of *Agrobacterium tumefaciens*, as well as those vectors described by Herrera-Estrella et al. (Nature 303 (1983), 209), Bevan (Nucl. Acids Res. 12 (1984), 8711–8721), Klee et al. (Bio/Technology 3 (1985), 637–642) and in EP-A2–120 516.

Transformation with the DNA molecules according to the invention is basically possible with cells of all plant species. Both monocotyledonous and dicotyledonous plants are of interest. For various monocotyledonous and dicotyledonous plants transformation techniques have already been described. Preferably, cells of ornamental or useful plants are transformed. The useful plants are preferably crop plants, particularly cereals (e.g., rye, oats, barley, wheat, maize, rice), potato, rape, pea, sugar beet, soy bean, tobacco, cotton, tomato, etc.

The invention furthermore relates to propagation material of a plant according to the invention, such as seeds, fruit, cuttings, tubers, root stocks, etc. containing the cells according to the invention.

The subject matter of the present invention is furthermore the use of DNA sequences coding for deregulated or unregulated FBPase enzymes for the expression in plant cells, preferably in the cytosol or the plastides, as well as for the production of plants which exhibit an increased photosynthesis rate and/or increased biomass production as compared to wild type plants.

The invention furthermore relates to a process for increasing the photosynthesis rate in plants which comprises the expression of DNA molecules in plant cells which code for a fructose-1,6-bisphosphate which is deregulated or unregulated in comparison to FBPases normally produced in plant cells.

FIG. 1 shows plasmid p35S-FBPase-Ae

A=fragment A: CaMV 35S promoter, nt 6909–7437 (Franck et al., Cell 21 (1980), 285–294)

B=fragment B: DNA from *Alcaligenes eutrophus* coding for the chromosomally encoded fructose-1,6-bisphosphatase;
1113 bp fragment having the DNA sequence depicted under Seq ID No. 1 orientation towards the promoter: sense C=fragment C: nt 11748–11939 of the T-DNA of the Ti plasmid pTiACH5 (Gielen et al., EMBO J. 3 (1984), 835–846)

The examples serve to illustrate the invention.

In the examples, the following techniques are used:

1. Cloning Techniques

For the cloning in *E. coli* the vector pUC18 was used. For the plant transformation the gene constructs were cloned into the binary vector pBinAR (Höfgen and Willmitzer, Plant Sci. 66 (1990), 221–230).

2. Bacterial Strains

For the pUC vectors and for the pBinAR constructs the *E. coli* strain DH5α (Bethesda Research Laboratories, Gaithersburgh, USA) was used.

Transformation of the plasmids in the potato plants was carried out by using *Agrobacterium tumefaciens* strain C58C1 pGV2260 (Deblaere et al., Nucl. Acids Res. 13 (1985), 4777–4788).

3. Transformation of *Agrobacterium tumefaciens*

Transfer of the DNA was carried out by direct transformation according to the method by Höfgen and Willmitzer (Nucleic Acids Res. 16 (1988), 9877). The plasmid DNA of transformed Agrobacteria was isolated according to the method by Birnboim and Doly (Nucleic Acids Res. 7 (1979), 1513–1523) and subjected to gel electrophoretic analysis after suitable restriction.

4. Transformation of Potatoes

Ten small leaves of a potato sterile culture (*Solanum tuberosum* L.cv. Désirée) were wounded with a scalpel and placed in 10 ml MS medium (Murashige and Skook, Physiol. Plant. 15 (1962), 473) containing 2% sucrose which contained 50 μl of a selectively grown overnight culture of *Agrobacterium tumefaciens*. After gently shaking the mixture for 3–5 minutes it was further incubated in the dark for 2 days. For callus induction the leaves were placed on MS medium containing 1.6% glucose, 5 mg/l naphthyl acetic acid, 0.2 mg/l benzyl aminopurine, 250 mg/l claforan, 50 mg/l kanamycin, and 0.80% Bacto agar. After incubation at 25° C. and 3,000 lux for one week the leaves were placed for shoot induction on MS medium containing 1.6% glucose, 1.4 mg/l zeatin ribose, 20 mg/l naphthyl acetic acid, 20 mg/l giberellic acid, 250 mg/l claforan, 50 mg/l kanamycin and 0.80% Bacto agar.

5. Radioactive Labelling of DNA Fragments

The DNA fragments were radioactively labelled using a DNA Random Primer Labelling Kit of Boehringer (Germany) according to the manufacturer's information.

6. Northern Blot Analysis

RNA was isolated according to standard techniques from leaf tissue of plants. 50 μg of RNA were separated in an agarose gel (1.5% agarose, 1×MEN buffer, 16.6% formaldehyde). The gel was shortly rinsed with water after gel run. The RNA was transferred with 20×SSC by capillary blot on a Hybond N nylon membrane (Amersham, UK). The membrane was then baked at 80° C. for two hrs in vacuo.

The membrane was prehybridized in NSEB buffer at 68° C. for 2 hrs and was then hybridized in NSEB buffer at 68° C. overnight in the presence of the radioactively labelled probe.

7. Plant Cultivation

Potato plants were cultivated in a greenhouse under the following conditions:

| | | |
|---|---|---|
| Light period | 16 hrs at 25,000 lux and 22° C. | |
| Dark period | 8 hrs at 15° C. | |
| Humidity | 60% | |
| Media and solutions used | | |
| 20 × SSC | 175.3 g | NaCl |
| | 88.2 g | sodium citrate |
| | ad | 1000 ml with ddH$_2$O |
| | pH | 7.0 with 10 N NaOH |
| 10 × MEN | 200 mM | MOPS |
| | 50 mM | sodium acetate |
| | 10 mM | EDTA |
| | pH | 7.0 |
| NSEB buffer | 0.25 M | sodium phosphate buffer pH 7.2 |
| | 7% | SDS |
| | 1 mM | EDTA |
| | 1% | BSA (wt./vol.) |

EXAMPLE 1

Construction of plasmid p35S-FBPase-Ae and introduction of the plasmid into the genome of potato plants A DNA fragment of 1136 bp length having the DNA sequence indicated under Seq ID No. 1 was isolated from a suitable plasmid using the restriction endonucleases NsiI and BalI.

This DNA fragment includes the whole coding region for the chromosomally encoded FBPase from *Alcaligenes eutrophus*. The cohesive ends were filled in using the T4-DNA polymerase and the fragment was inserted into the vector pBinAR (Höfgen and Willmitzer, Plant Sci. 66 (1990), 221–230) which had been linearized with SmaI. The vector pBinAR is a derivative of the binary vector Bin19 (Bevan, Nucleic Acids Res. 12 (1984), 8711–8721; commercially available from Clontech Laboratories, Inc., USA).

pBinAR was constructed as follows:

A fragment of 529 bp length comprising nucleotides 6909–7437 of the 35S promoter of the cauliflower mosaic virus (Franck et al., Cell 21 (1980), 285–294) was isolated as EcoRI/KpnI fragment from plasmid pDH51 (Pietrzak et al., Nucl. Acids Res. 14, 5857–5868) and ligated between the EcoRI and KpnI restriction sites of the polylinker of pBin19, resulting in plasmid pBin19-A.

A fragment of 192 bp length was isolated from plasmid pAGV40 (Herrera-Estrella et al., Nature 303, 209–213) using the restriction endonucleases PvuII and HindIII, which fragment comprises the polyadenylation signal of gene 3 of the T-DNA of Ti plasmid pTiACH5 (Gielen et al., EMBO J. 3, 835–846) (nucleotides 11749–11939). After addition of SphI linkers to the PvuI restriction site the fragment was ligated into pBin19-A which had been cleaved with SphI and HindIII, resulting in pBinAR.

The DNA fragment was inserted into the vector such that the coding region was in sense-orientation towards the 35S promoter.

The resulting plasmid was called p35S-FBPase-Ae and is depicted in FIG. 1.

Insertion of the DNA fragment results in an expression cassette that is composed of fragments A, B and C as follows (FIG. 1):

Fragment A (529 bp) contains the 35S promoter of the cauliflower mosaic virus (CaMV). The fragment comprises nucleotides 6909 to 7437 of CaMV (Franck et al., Cell 21 (1980), 285–294).

Fragment B comprises the protein-encoding region of the chromosomally encoded FBPase from *Alcaligenes eutrophus*. This fragment was isolated as NsI/BalI fragment as described above and fused to the 35S promoter in pBinAR in sense orientation.

Fragment C (192 bp) contains the polyadenylation signal of gene 3 of the T-DNA of Ti plasmid pTiACH5 (Gielen et al., EMBO J. 3 (1984), 835–846).

The size of the plasmid p35S-FBPase-Ae is about 12 kb. Vector p35S-FBPase-Ae was transferred to potato plant cells via *Agrobacterium tumefaciens*-mediated transformation. Intact plants were regenerated from the transferred cells. Success of the genetic modification of the plants is verified by subjecting the total RNA to a northern blot analysis with respect to the synthesis of an mRNA coding for the FBPase from *A. eutrophus*. Total RNA is isolated from leaves of transformed plants according to standard techniques, separated on an agarose gel, transferred to a nylon membrane and hybridized to a radioactively labelled probe exhibiting the sequence depicted under Seq ID No. 1 or part of said sequence. Successfully transformed plants exhibit a band in northern blot analysis that indicates the specific transcript of the FBPase gene from *Alcaligenes eutrophus*.

EXAMPLE 2

Analysis of Transformed Potato Plants

Potato plants that had been transformed with the plasmid p35S-FBPase-Ae were examined for their photosynthesis rate as compared to non-transformed plants.

The photosynthesis rates were measured with leaf disks in a leaf disk oxygen electrode (LD2; Hansatech; Kinks Lynn, England). The measurement was performed under a saturated CO$_2$ atmosphere at 20° C. as described by Schaewen et al. (EMBO J. 9 (1990), 3033–3044). Light intensity was 550–600 PAR (photosynthetic active radiation).

The results of such a measurement of the photosynthesis rate of plants that were transformed with the plasmid p35S-FBPase-Ae (UF1-7) in comparison with that of non-transformed plants is shown in the following table.

| Plant | photosynthesis rate [mmol O$_2$ × (m$^2$ × h)$^{-1}$] | % |
|---|---|---|
| Wild type | 48 ± 6.1 | 100 ± 12.7 |
| UF1-7 (p35S-FBPase-Ae) | 67 ± 6.3 | 140 ± 13.1 |

For wild type plants ten measurements were performed while for the transformed potato plants UF1-7 five measurements were made.

What is claimed is:

1. An isolated recombinant DNA molecule comprising
   (a) a promoter functional in plant cells, and
   (b) a heterologous DNA sequence linked to said promoter in sense orientation, said DNA sequence coding for a polypeptide having the enzymatic activity of a fructose-1,6-bisphosphatase (FBPase),
   wherein said FBPase is subject to reduced inhibition by fructose-2,6-bisphosphate or AMP compared to a cytosolic plant FBPase.

2. The DNA molecule according to claim 1, wherein the DNA sequence originates from a procaryotic organism or is derived from said DNA sequence.

3. The DNA molecule according to claim 1, wherein the procaryotic organism is *Alcaligenes eutrophus*.

4. The DNA molecule according to claim 1, wherein the DNA sequence has the nucleotide sequence of SEQ ID NO: 1 from the nucleotide at position 30 to the nucleotide at position 1121, or a fragment thereof having FBPase activity.

5. The DNA molecule according to claim 1, wherein the DNA sequence originates from a plant, an animal organism or a fungus, or is derived from said DNA sequence.

6. A transgenic plant cell comprising the DNA molecule according to claim 1.

7. A transgenic plant comprising the plant cell according to claim 6.

8. The plant according to claim 7 which is an ornamental plant.

9. The plant according to claim 7 which is a useful plant.

10. Propagation material of the plant according to claim 7.

11. The DNA molecule according to claim 1, wherein said DNA sequence, when expressed in a plant cell, encodes a polypeptide located in the cytosol of said plant cell.

12. A method for expressing a polypeptide encoded by the DNA molecule according to any one of claims 1 to 5 or claim 11, comprising the steps of introducing the DNA molecule into a plant cell and expressing the DNA molecule.

13. The method according to claim 12, wherein the expression of said polypeptide results in an increase in photosynthesis rate, an increase in biomass production or both.

14. A method for increasing the biomass production of a plant, comprising the step of expressing a polypeptide encoded by the DNA molecule according to claim 1 in a transgenic plant.

15. The transgenic plant cell according to claim 6, wherein expression of a polypeptide encoded by said DNA molecule results in an increase in photosynthesis rate, an increase in biomass production or both.

16. The transgenic plant according to claim 7, wherein expression of a polypeptide encoded by said DNA molecule results in an increase in photosynthesis rate, an increase in biomass production or both.

17. A method for increasing the photosynthesis rate in a plant comprising the step of expressing a polypeptide encoded by the DNA molecule according to claim 1 in a transgenic plant.

18. A method for increasing the photosynthesis rate and biomass production in a plant, comprising the step of expressing a polypeptide encoded by the DNA molecule according to claim 1 in a transgenic plant.

19. A method for increasing the photosynthesis rate in a plant cell, comprising the step of expressing a polypeptide encoded by the DNA molecule according to claim 1 in a transgenic plant cell.

20. A method for increasing the photosynthesis rate and biomass production in a plant cell, comprising the step of expressing a polypeptide encoded by the DNA molecule according to claim 1 in a transgenic plant cell.

* * * * *